United States Patent
Paufique

(12) 
(10) Patent No.: US 6,531,132 B1
(45) Date of Patent: Mar. 11, 2003

(54) PROCESS FOR THE EXTRACTION OF AN ACTIVE PRINCIPLE FROM YEAST FOR THE TREATMENT OF WRINKLES AND COSMETIC COMPOSITIONS THEREOF

(75) Inventor: Jean-Jacques Paufique, Objat (FR)

(73) Assignee: Societe Industrielle Limousine d'Application Biologique (SILAB), Objat (FR)

( * ) Notice: Subject to any disclaimer, the term of this patent is extended or adjusted under 35 U.S.C. 154(b) by 0 days.

(21) Appl. No.: 09/630,611

(22) Filed: Aug. 2, 2000

(30) Foreign Application Priority Data

Aug. 2, 1999 (FR) .............................. 99 10152

(51) Int. Cl.[7] .................. A61K 35/00; A61K 6/00; C12N 1/14
(52) U.S. Cl. ............... 424/195.6; 424/78.02; 424/78.03; 424/401; 435/254.21; 514/844; 514/847
(58) Field of Search ................ 435/254.21, 254.1; 424/195.16, 115, 78.02, 78.03, 401; 514/844, 847

(56) References Cited

U.S. PATENT DOCUMENTS

| | | |
|---|---|---|
| 2,320,478 A | * 6/1943 | Sperti |
| 4,698,166 A | 10/1987 | Danner et al. |
| 4,810,509 A | 3/1989 | Kanegae et al. |
| 5,019,391 A | 5/1991 | Bunte et al. |
| 5,055,298 A | * 10/1991 | Kludas |
| 5,238,925 A | * 8/1993 | Bentley |
| 5,676,956 A | 10/1997 | Duffy et al. |
| 6,146,857 A | * 11/2000 | Pauly et al. |

FOREIGN PATENT DOCUMENTS

| | | |
|---|---|---|
| AU | 509965 | 6/1980 |
| EP | 0 695 801 | 2/1996 |
| WO | WO 91 02533 | 3/1991 |
| WO | WO 97/21828 | * 6/1997 |

* cited by examiner

*Primary Examiner*—Christopher R. Tate
*Assistant Examiner*—Michele C. Flood
(74) *Attorney, Agent, or Firm*—Young & Thompson

(57) ABSTRACT

A process for extracting an active principle from yeast whereby the active principle is used to retard the degradation of the dermo-epidermal junction to improve the surface condition of the skin. The process includes forming a mixture of solubilized ground yeast in a basic medium, hydrolyzing the proteins of the mixture in a basic medium, agitating the mixture for 8 to 52 hours, filtering the mixture to separate the soluble and insoluble phases, washing with water so as to purify the active ingredient, concentrating and filtering to increase an active oligosaccharide fraction, and sterile filtering the active fraction. The active fraction is characterized by a quantity of dry material between 10 and 200 g/l, a quantity of total sugar between 10 and 100 g/l, a weight ratio of sugar/protein, and a pH between 4 and 10.

20 Claims, 3 Drawing Sheets

Figure 4A:
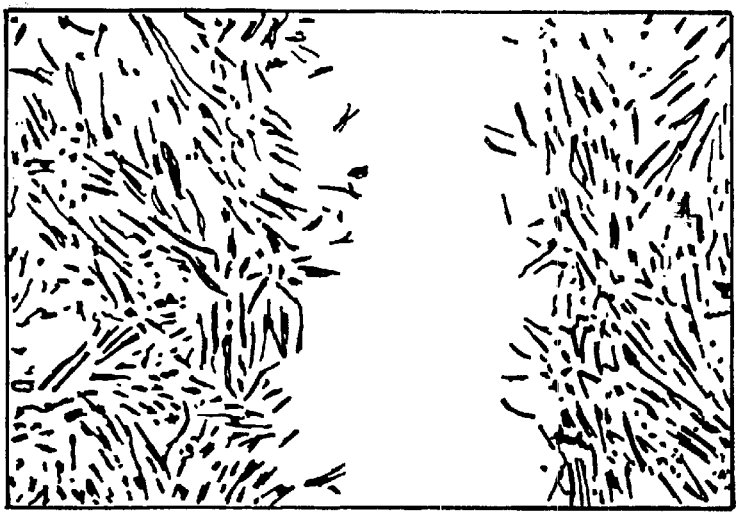

|  |  | Collagen IV | Collagen VII | Fibronectine |
|---|---|---|---|---|
| Yeast Extract | RT | 0.97 | 0.48 | 1.61 |
|  | RE | 1.43 | 0.65 | 1.93 |
|  | % ARNm/control | 147 % | 135 % | 120 % |

FIG. 1

| Time of incubation | Integrines $\beta 1$ | | Integrines $\alpha 2$ | |
|---|---|---|---|---|
|  | Control | Yeast extract | Control | Yeast extract |
| 24 hours | 100 % | 130 % | 100 % | 198 % |
| 48 hours | 100 % | 164 % | 100 % | 230 % |

FIG. 2

| Time of incubation |  | | Yeast extract | | |
|---|---|---|---|---|---|
|  |  | Control | 0.5 % | 1 % | 2 % |
| $T_1$ | % | 100 % | 139 % | 88 % | 115 % |
| $T_2$ | % | 100 % | 140 % | 138 % | 149 % |
| $T_3$ | % | 100 % | 134 % | 128 % | 129 % |

FIG. 3

| Complexity of the microprofile in % | | | | | | |
|---|---|---|---|---|---|---|
| Active principle | | | Placebo | | | |
| J0 | J28 | Δ(J28-J0) | J0 | J28 | Δ(J28-J0) | ΔΔ(FO-PL) |
| Average | 3.73 | 3.55 | -0.18 | 3.67 | 4.58 | 0.71 | -0.89 |
| Δ % | -20 | | | | | |

FIG. 5

| Complexity of the surfaces in % | | | | | | |
|---|---|---|---|---|---|---|
| Active principle | | | Placebo | | | |
| J0 | J28 | Δ(J28-J0) | J0 | J28 | Δ(J28-J0) | ΔΔ(FO-PL) |
| Average | 11.75 | 8.92 | -2.83 | 8.97 | 11.63 | 2.66 | -5.49 |
| Δ % | -38 | | | | | |

FIG. 6

| Maximum depth in mm | | | | | | |
|---|---|---|---|---|---|---|
| Active principle | | | Placebo | | | |
| J0 | J28 | Δ(J28-J0) | J0 | J28 | Δ(J28-J0) | ΔΔ(FO-PL) |
| Average | 0.313 | 0.269 | -0.044 | 0.282 | 0.309 | 0.027 | -0.071 |
| Δ % | -21 | | | | | |

FIG. 7

| Volume in mm$^3$ | | | | | | |
|---|---|---|---|---|---|---|
| Active principle | | | Placebo | | | |
| J0 | J28 | Δ(J28-J0) | J0 | J28 | Δ(J28-J0) | ΔΔ(FO-PL) |
| Average | 0.626 | 0.507 | -0.119 | 0.585 | 0.585 | -0.001 | -0.118 |
| Δ % | -19 | | | | | |

FIG. 8

PROCESS FOR THE EXTRACTION OF AN ACTIVE PRINCIPLE FROM YEAST FOR THE TREATMENT OF WRINKLES AND COSMETIC COMPOSITIONS THEREOF

The present invention relates to a process for the extraction of an active principle from at least one yeast for treatment against aging of the skin and particularly to guard against the appearance of wrinkles.

The invention also covers the active principle obtained, the cosmetic compositions which include it as well as the treatment envisaged with this active principle.

There exists a so-called dermo-epidermal junction which constitutes an interface between the derma and the epidermis.

This region is very complicated and performs several particular functions which are involved in the various biological processes such as tissue repair, attachment or differentiation of the epidermal cells.

Thus, the dermo-epidermal junction promotes exchanges between the derma and the epidermis, and takes part actively in epidermal communication.

This dermo-epidermal junction also plays a very important role in the "mechanical", cohesion between the derma and the epidermis, thanks to specific anchoring molecules, namely:

IV and VII collagens integrines, fibernectine.

Thus, the dermo-epidermal junction comprises essentially the basal epidermal membrane, the anchoring febriles and the hemidesmosomes. However, this basal membrane has a high mechanical resistance, due particularly to the pulmerization of this fibrous protein which is collagen IV, present in the form of dimers and tetramers.

Collagen VII itself is the major component of the anchoring febriles. Collagen VII can connect to the end-terminal ends of collagen IV and of fibronectin to form a network.

The integrines are glycoproteins whose surface is constituted of two sub-units $\alpha$ and $\beta$. These integrines are specific as to function of the cellular type which express them. The culture cells express particularly the integrines $\alpha_2\beta_1$, $\alpha_3\beta_1$ and $\alpha_5\beta_1$.

The integrines $\alpha_2\beta_1$, expressed by keratinocytes and fibroblasts, represent cellular receptors for the type IV collagens as well as fibronectine. These integrines play an important role in maintaining a spatial organization of the dermo-epidermal junction and in the repair/scabbing phenomena.

It is on the quality of the anchorages and hence the connections at the dermo-epidermal junction that the surface condition of the skin depends.

Thus, if the dermo-epidermal junction is strong, with folds ensuring an excellent cohesion between the derma and the epidermis, the skin is slightly wrinkled, whilst any relaxation due to a synthesis of a smaller quantity of anchoring molecules gives rise to a flattening of the interface with a loss of firmness and regularity of the surface of the skin.

The present invention also has for its object to provide an active principle which permits guarding against the effects of cutaneous aging with a deep action, by stimulating the synthesis of the anchoring molecules such as the integrines, the fibronectine and the collagens IV and VII, which promotes maintaining the dermo-epidermal cohesion and tissue repair. Because of this, the depth of the wrinkles decreases and the microcontour of the skin is smooth.

The invention also has for its object the extraction process as well as the cosmetic treatments which consist in using this active principle in a cosmetic composition.

Figure 4B:
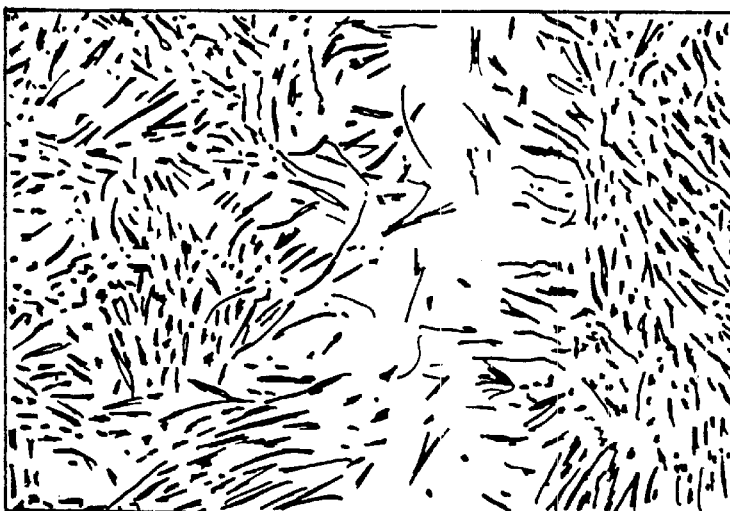
Figure 4C:
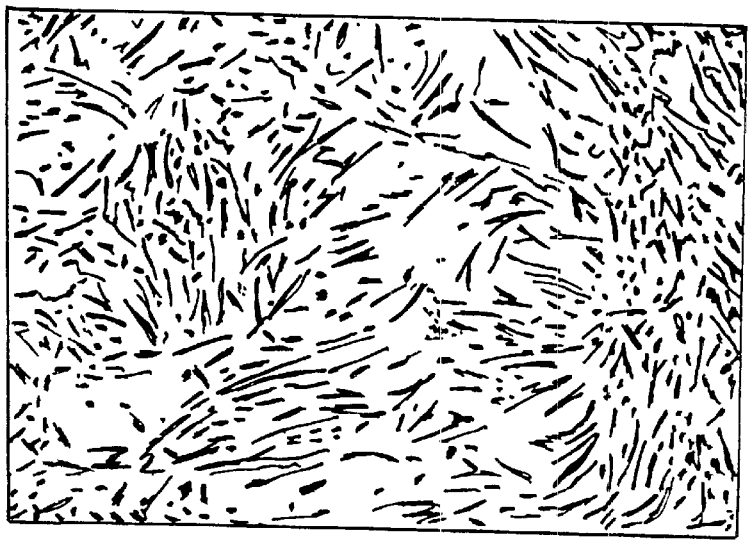

The different tables and results and the microscopic views are indicated in the figures, which show:

FIG. 1, evaluation of the expression of the ARN messengers of the anchoring molecules relative to a control, FIG. 2, evaluation of the expression of the integrines, FIG. 3, effects of the active principle on the migration of fibroblasts, FIGS. 4A, 4B and 4C, microscopic views of the effects of the active principle on the migration of the fibroblasts, FIG. 5, results relating to the complexity of the microrelief, FIG. 6, results concerning the complexity of the surface, FIG. 7, results of the development of the depths of wrinkles, and FIG. 8, results of the development of the volume of wrinkles.

The active principle according to the present invention will now be described beginning with its process for extraction and its characteristics, by showing the effects obtained on the different mechanisms taking place at the dermo-epidermal junction.

The process of extraction of the active principle according to the present invention consists in using a yeast, in particular *Saccharomyces Cerevisiae*.

This process comprises the following steps:

solubilization of the ruptured yeast cells in slightly basic aqueous medium in the amount of at least 20% with, if desired, the addition of an alcohol so as to promote solubilization of the yeast, at low temperature of the order of 4° C. for 5 hours, enzymatic hydrolysis of the proteins in basic medium with the addition of enzymes in the amount of 0.01% to 5% by volume. This hydrolysis ensures the cutting of the proteins into small peptides which are then easier to eliminate during washing and concentration, agitation for 8 to 52 hours, first filtration so as to separate the soluble and insoluble phases, washing with water so as to purify the active fraction from salts, proteins and peptides, successive concentrations and filtrations so as to increase the active fraction, of the oligosaccharidic type and sterilizing filtration.

In the case of *Saccharomyces Cerevisiae*, the active principle thus obtained is characterized by the following analytical parameters:

Weight of dry material: comprised between 10 g/l and 200 g/l more particularly between 10 and 100 g/l, principally between 20 and 50 g/l. This weight is obtained by passage through an oven at 105° C. until a constant weight is obtained.

Total sugars: comprised between 10 g/l and 100 g/l, more particularly between 10 and 70 g/l, principally between 20 and 50 g/l.

The determination of total sugar is carried out according to the DUBOIS method. There is added to the active principle 400 µl of 5% phenol and 2000 µl of sulfuric acid.

The optical density of the solution is then read spectrophotometrically at 490 nm. The same experiment is carried out with a standard range from 25 to 100 µg/ml of a solution of mannose, glucose and galactose.

the weight ratio of sugars/proteins must be from 60 at the minimum, better 70 at the minimum.

pH comprised between 4 and 10, more particularly 6 to 7. This parameter is measured by the potentiometric method at ambient temperature.

1/ EVALUATION OF THE EXPRESSION OF RNA MESSENGERS OF THE ANCHORING MOLECULES

The action of the obtained active principle is studied on human fibroblast cultures.

These fibroblasts are cultured for 72 hours at 37° C. in an atmosphere containing 5% $CO_2$, in the presence of the product.

At the end of incubation, the cells are recovered and the total RNA is extracted. The RNA were reverse-transcripts and the complementary DNA obtained has been analyzed by chain polymerase techniques.

Concurrently, the mRNA of the β-actine is also analyzed under the same experimental conditions as a control. The intensity of the bands of amplicons on agarose gel are measured, with an image analyzer.

The results are expressed in percentage of expression of the RNA studied for each test relative to the control, according to the following ratio:

$$\%mRNA/control=(R.E./R.T.)\times 100$$

R.E.=intensity of the mRNA band of the tested protein/intensity of the mRNA band of the β-actine R.T.=intensity of the mRNA band of the control protein/intensity of the mRNA band of the β-actine There are obtained the results shown in the table of FIG. 1, obtained with 2% active principle. There is seen an increase of the expression of mRNA of the IV and VIII collagens and the fibronectine in the human fibroblast cultures.

It will be seen that the active principle induces the secretion of anchoring proteins of the dermo-epidermal junction, particularly IV and VII collagens as well as fibronectine.

2/ MEASUREMENT OF THE MEMBRANE EXPRESSION OF INTEGRINES

It is sought to evaluate a cytometry of the flow, the membrane expression of the integrines $\alpha_2\beta_1$ on the human fibroblast cultures after 24 and 48 hours of incubation in the presence of 3% of the active principle.

The cells are marked with monoclonal antibodies directed specifically against the type $\alpha_2$ or $\beta_1$ integrines.

These antibodies are marked with a second marked fluorescent antibody. The level of membrane expression is determined by measurement of the fluorescence and analyzed by flow cytometry.

The results are expressed as the percentage of increase of the number of fluorescent sites relative to an untreated control. They are given in Table 2 of FIG. 2.

It will be seen that 3% of active principle promotes the synthesis of the $\alpha_2\beta_1$ integrines responsible for the cohesion of the dermo-epidermal junction and the cellular interactions.

3/ EVALUATION OF THE EFFECTS OF THE ACTIVE PRINCIPLE ON THE MIGRATION OF FIBROBLASTS

Human fibroblasts are incubated in a culture medium of fibroblasts to which has been added the mitomycin C whose role is to block cellular divisions such that there is studied only the capability of these cells to migrate.

This test is conducted on a monolayer culture of human fibroblasts on a glass plate, in which layer there has been carried out a cutting for example by scalpel, so as to give rise to a linear region in which there are no more cells.

This cut at the moment T0 is free from cells.

There is microscopically determined the development of the number of cells present in the cut region, in the course of time until repair.

The active principle is introduced into the culture medium at concentrations of 0.5%, 1% and 2%.

The results of the counts are indicated in the table of FIG. 3, at T1=24, T2=48 and T3=72 hours.

FIGS. 4A, 4B and 4C show microscopic views of the cut region and of the increasing density of the cells in the course of time T0 to T3.

It will be noted that the active principle stimulates the migration of fibroblasts. Notice that the action of the active principle is immediate even at low content.

4/ STUDIES OF THE EFFECTS ON VOLUNTEERS

The test is conducted on 15 volunteers, of female gender and a mean age of 48. This test is carried out with an emulsion containing 5% of active principle, against a placebo.

Impressions are taken at the level of the two crow's-feet, which is to say the outer side region about the eyes which comprises lines and wrinkles arising from squinting. These impressions are made at day 1 (beginning of the test) and at 28 days.

The parameters studied as to wrinkles are the following:
for a smoothing effect: complexity of the cutaneous microprofile,
for an anti-wrinkle effect:—complexity of the surface, maximum depth of the wrinkle (in mm), and volume of the wrinkle (in $mm^3$)

Statistical analysis of the data permits determining the significant effect of the obtained variations. The test used is the Student test on matched data.

It will be noted from the following differences the variations of the different parameters of the cutaneous profile in the retained zones treated with the active principle Pr and with the placebo Pl.

$$\Delta r = Pr_{J28} - Pr_{J0}$$

$$\Delta r = Pl_{J28} - Pl_{J0}$$

the variations between the two regions therefore are:

$$\Delta r - \Delta l = (Pr_{J28} - Pr_{J0}) - (Pl_{J28} = Pl_{J0})$$

From the means, there is used the following formula:

$$\Delta\% = (Pr_{J28} - Pr_{J0}) - (Pl_{J28} - Pl_{J0})/(Pl_{J28} - Pl_{J0}) + Pr_{J0} \times 100$$

the results relating to complexity of the microprofile are collected in the table of FIG. 5.

There is seen a decrease of 20% of the complexity of the cutaneous microprofile. This smoothing effect is observed in 80% of the volunteers.

The results concerning the study of wrinkles are gathered in the tables of FIGS. 6, 7 and 8.

There is seen a decrease of 38% of the complexity of the surface. This effect is observed in 73% of the volunteers.

There is seen a decrease of 21% of the depth of the wrinkles. This effect is observed in 67% of the volunteers.

Finally, there is seen a decrease of 19% of the volume of the wrinkles in 60% of the volunteers.

Thus, the active principle according to the present invention improves very substantially the qualities of the dermo-epidermal junction, which has significant effect on the condition of the surface of the skin.

The active principle can be used by introduction into any cosmetic preparation, no matter whether of galenic, cream, emulsion, or solution form.

So as to permit guarding against degradation of the surface condition of the skin, the present invention provides use of a product containing a quantity of 2 to 7% of active principle in the regions in question, for periods of the order of 28 days.

What is claimed is:

1. A process for extracting an active principle to guard against degradation of a dermo-epidermal junction of skin and to improve the surface condition of skin, comprising:
   solubilizing crushed *Saccharomyces Cerevisiae* in a basic aqueous medium to form a mixture,
   hydrolyzing proteins of the mixture in a basic medium by adding enzymes in the amount of 0.05% to 5% by volume,
   agitating the mixture,
   filtering the mixture to separate soluble and insoluble phases,
   obtaining an oligosaccharide active fraction,
   washing with water said oligosaccharide active fraction so as to purify said oligosaccharide active fraction from salts, proteins and peptides,
   concentrating and filtering said oligosaccharide active fraction to obtain an active principle, and
   sterile filtering said active principle.

2. The process according to claim 1, further comprising adding alcohol to the solubilizing step to promote solubilization.

3. The process according to claim 1, wherein the solubilizing step is conducted at a temperature of 4° C. for 5 hours.

4. The process according to claim 1, further comprising adding alcohol to the solubilizing step to promote solubilization and wherein the solubilizing step is conducted at a temperature of 4° C. for 5 hours.

5. The process according to claim 1, wherein said agitating step is conducted for 8 to 52 hours.

6. An active principle obtained by the process according to claim 1, comprising:
   a quantity of dry material between 10 and 200 g/L,
   a quantity of total sugar between 10 and 100 g/L,
   a weight ratio of sugar/proteins of at least 60, and
   a pH between 4.0 and 10.0.

7. An active principle obtained by the process according to claim 1, comprising:
   a quantity of dry material between 10 and 100 g/L,
   a quantity of total sugar between 10 and 70 g/L,
   a weight ratio of sugar/proteins of at least 70, and
   a pH between 6.0 and 7.0.

8. An active principle obtained by the process according to claim 1, comprising:
   a quantity of dry material between 20 and 50 g/L,
   a quantity of total sugar between 20 and 50 g/L, and
   a pH between 6.0 and 7.0.

9. A cosmetic composition comprising an active principle obtained by the process according to claim 1, in admixture with a cosmetologically acceptable excepient.

10. The cosmetic composition according to claim 9, wherein the active principle is added to the cosmetic in an amount of 2 to 7%.

11. The cosmetic composition according to claim 9, wherein the cosmetic composition is selected from the group consisting of galenic, cream, emulsion or solution form.

12. An active principle obtained by the process according to claim 1.

13. A process for extracting an active principle to guard against degradation of dermo-epidermal junction of skin and to improve the surface condition of skin, comprising:
   solubilizing crushed *Saccharomyces Cerevisiae* in a basic aqueous medium to form a mixture, wherein said mixture contains at least 20% *Saccharomyces Cerevisiae*,
   hydrolyzing proteins of the mixture in a basic medium by adding enzymes in the amount of 0.05% to 5% by volume,
   agitating the mixture,
   filtering the mixture to separate soluble and insoluble phases,
   obtaining an oligosaccharide active fraction,
   washing with water said oligosaccharide fraction so as to purify said oligosaccharide active fraction from salts, proteins and peptides,
   concentrating and filtering said oligosaccharide active fraction,
   obtaining an active principle, and
   sterile filtering said active principle.

14. The process according to claim 13, further comprising adding alcohol to the solubilizing step to promote solubilization.

15. The process according to claim 13, wherein the solubilizing step is conducted at a temperature of 4° C. for 5 hours.

16. The process according to claim 13, further comprising adding alcohol to the solubilizing step to promote solubilization and the solubilizing step is conducted at a temperature of 4° C. for 5 hours.

17. An active principle obtained by the process according to claim 13, comprising:
   a quantity of dry material between 10 and 200 g/L,
   a quantity of total sugar between 10 and 100 g/L,
   a weight ratio of sugar/proteins of at least 60, and
   a pH between 4.0 and 10.0.

18. A process for extracting an active principle to guard against degradation of dermo-epidermal junction of skin and to improve the surface condition of skin, comprising:
   solubilizing crushed *Saccharomyces Cerevisiae* in a basic aqueous medium to form a mixture,
   hydrolyzing proteins of the mixture in a basic medium by adding enzymes in the amount of 0.05% to 5% by volume,
   filtering the mixture to separate soluble and insoluble phases,
   obtaining an oligosaccharide active fraction,
   washing with water said oligosaccharide active fraction so as to purify said oligosaccharide active fraction from salts, proteins and peptides,
   concentrating and filtering said oligosaccharide active fraction.

19. The process according to claim 18, further comprising adding alcohol to the solubilizing step to promote solubilization and wherein the solubilizing step is conducted at a temperature of 4° C. for 5 hours.

20. An active principle obtained by the process according to claim 18, comprising:
   a quantity of dry material between 10 and 200 g/L,
   a quantity of total sugar between 10 and 100 g/L,
   a weight ratio of sugar/proteins of at least 60, and
   a pH between 4.0 and 10.0.

* * * * *